United States Patent [19]
Lopez et al.

[11] Patent Number: 5,720,046
[45] Date of Patent: Feb. 24, 1998

[54] ARTICLES OF HUMANWEAR MERCHANDISE HAVING MAGNETIC STRUCTURE FOR PRODUCING MAGNETIC HEALING EFFECTS

[76] Inventors: Richard A. Lopez, 4001 W. Redwing St., Tucson, Ariz. 85741; Augustine C. Fong, 920 S. Craycroft, Tucson, Ariz. 85711

[21] Appl. No.: 496,686

[22] Filed: Jun. 29, 1995

[51] Int. Cl.$^6$ .............. A61N 2/08; A41D 19/00
[52] U.S. Cl. .............. 2/159; 2/160; 600/15
[58] Field of Search .............. 2/160, 163, 16, 2/159, 161.1, 161.6, 161.7, 167; 600/15, 9, 13, 14; 335/302, 303, 219; 606/204

[56] References Cited

U.S. PATENT DOCUMENTS

| | | | |
|---|---|---|---|
| 3,635,190 | 1/1972 | Araki | 2/161.4 |
| 3,636,568 | 1/1972 | Stuner | 2/161.6 |
| 4,006,900 | 2/1977 | DiVito | 2/19 |
| 4,162,672 | 7/1979 | Yazaki | 600/15 |
| 4,240,157 | 12/1980 | Peters | 2/161.6 |
| 4,509,219 | 4/1985 | Yagi | 5/481 |
| 4,921,560 | 5/1990 | Yamaguchi | 156/213 |
| 5,085,626 | 2/1992 | Frey | 600/15 |
| 5,093,933 | 3/1992 | Berry | 2/163 |
| 5,304,111 | 4/1994 | Mitsuno et al. | 600/15 |
| 5,405,310 | 4/1995 | Yoo | 601/134 |
| 5,448,777 | 9/1995 | Lew | 2/161.7 |

FOREIGN PATENT DOCUMENTS

| | | | |
|---|---|---|---|
| 3823 | 12/1872 | Germany | 600/15 |
| 340184 | 9/1959 | Switzerland | 2/161.6 |

OTHER PUBLICATIONS

Japan Life Products, p. 11, OMS Medical Supplies 1992–93 Catalog pp. 59, 62, 63,64,66.
Undated Japan Life Article Entitled: Spreading Good Sleep Around the World.
Undated Japan Life Article Entitled: Complete Body Support LHASA Medical Supplie, Inc.
1995 Product Invoice, LHASA Medical Supplies.
OMS Medical Supplies, 1992–93, Catalog pp. 59,62,63,64, 66.

*Primary Examiner*—Amy B. Vanatta

[57] ABSTRACT

Humanwear merchandise is provided in the form of torso-worn garments, headgear and gear for body appendages. The merchandise includes magnetic structure that corresponds to acupressure points on the human torso, head and body appendages for effecting therapeutic magnetic exposure when worn by a human user. The magnet-containing human-wear merchandise includes: (1) several glove designs, (2) torso-worn garments, including T-shirts, pants, briefs, and brassieres, and (3) headgear and various gear for body appendages, including a facemask, a visored-headband, footwear, ankle/foot band support, wrist/hand band supports, finger band, neck band support, and localized elbow and knee support bands.

16 Claims, 8 Drawing Sheets

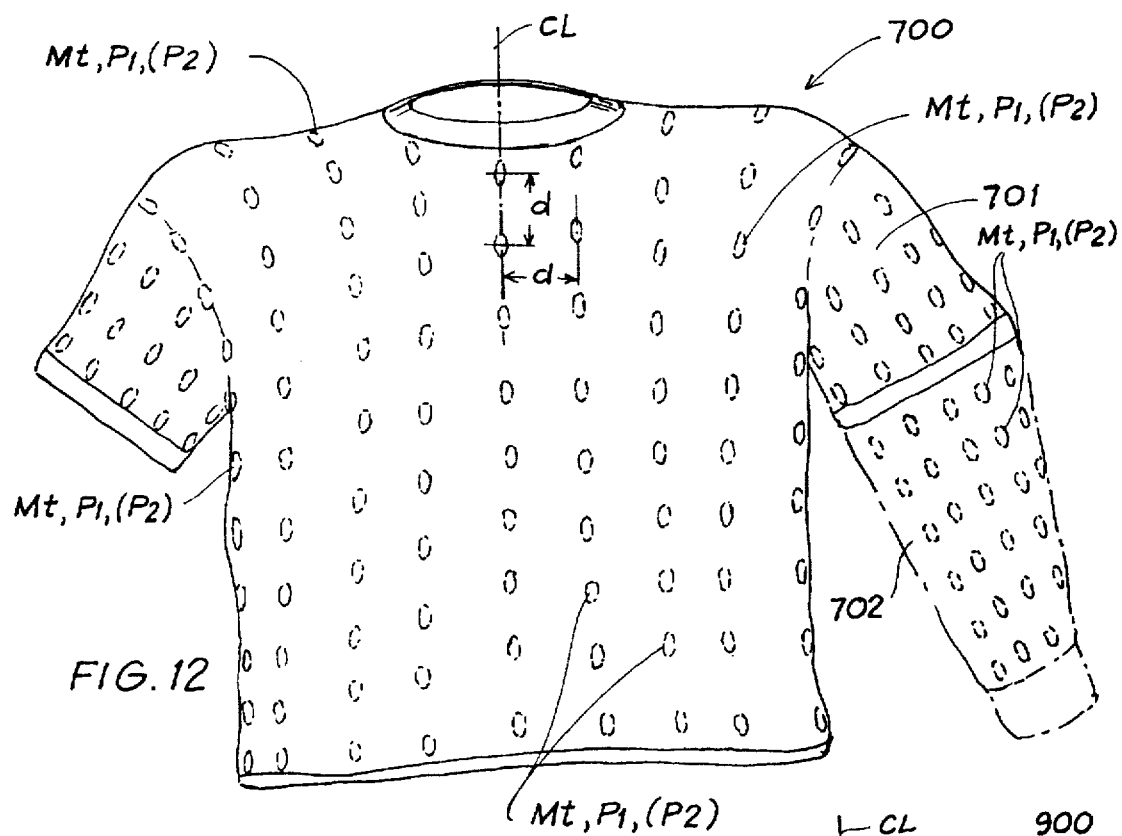
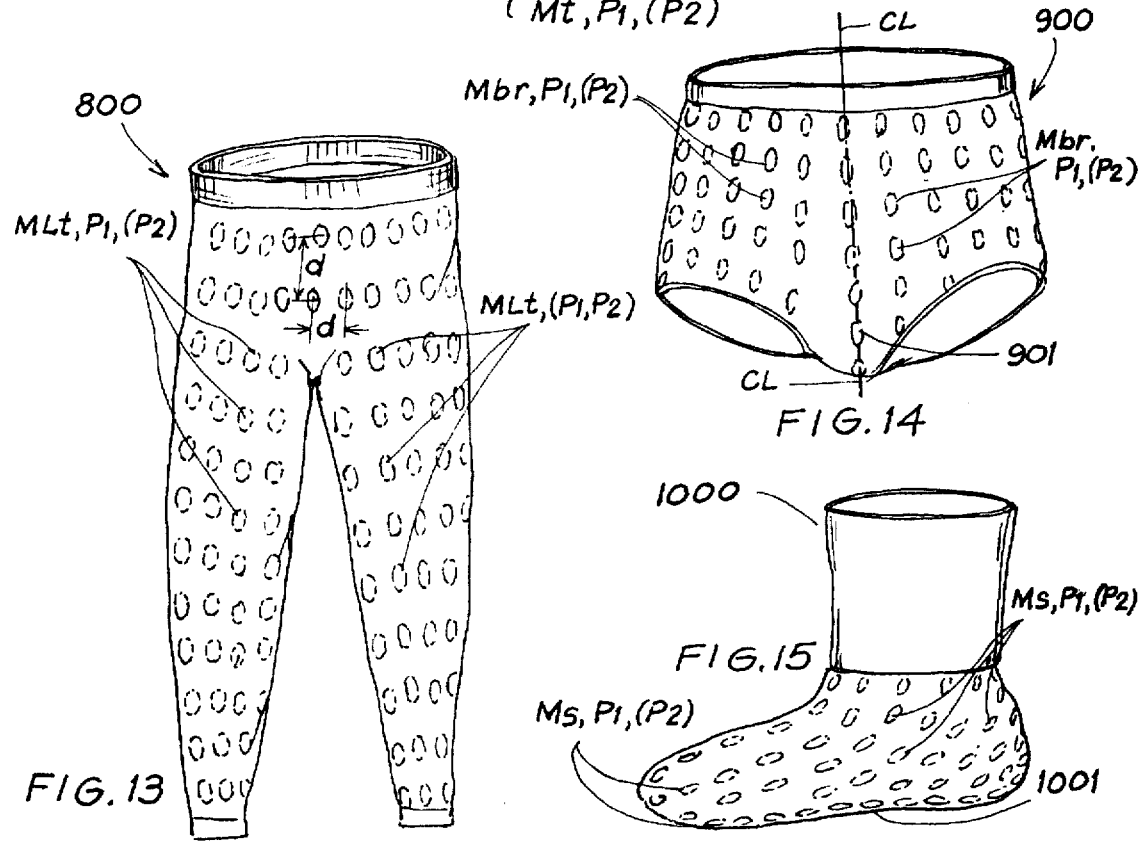
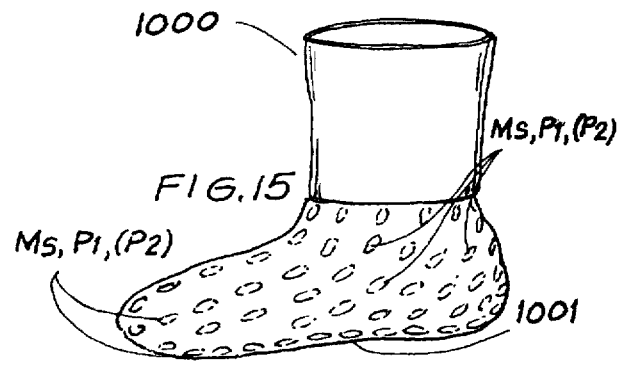

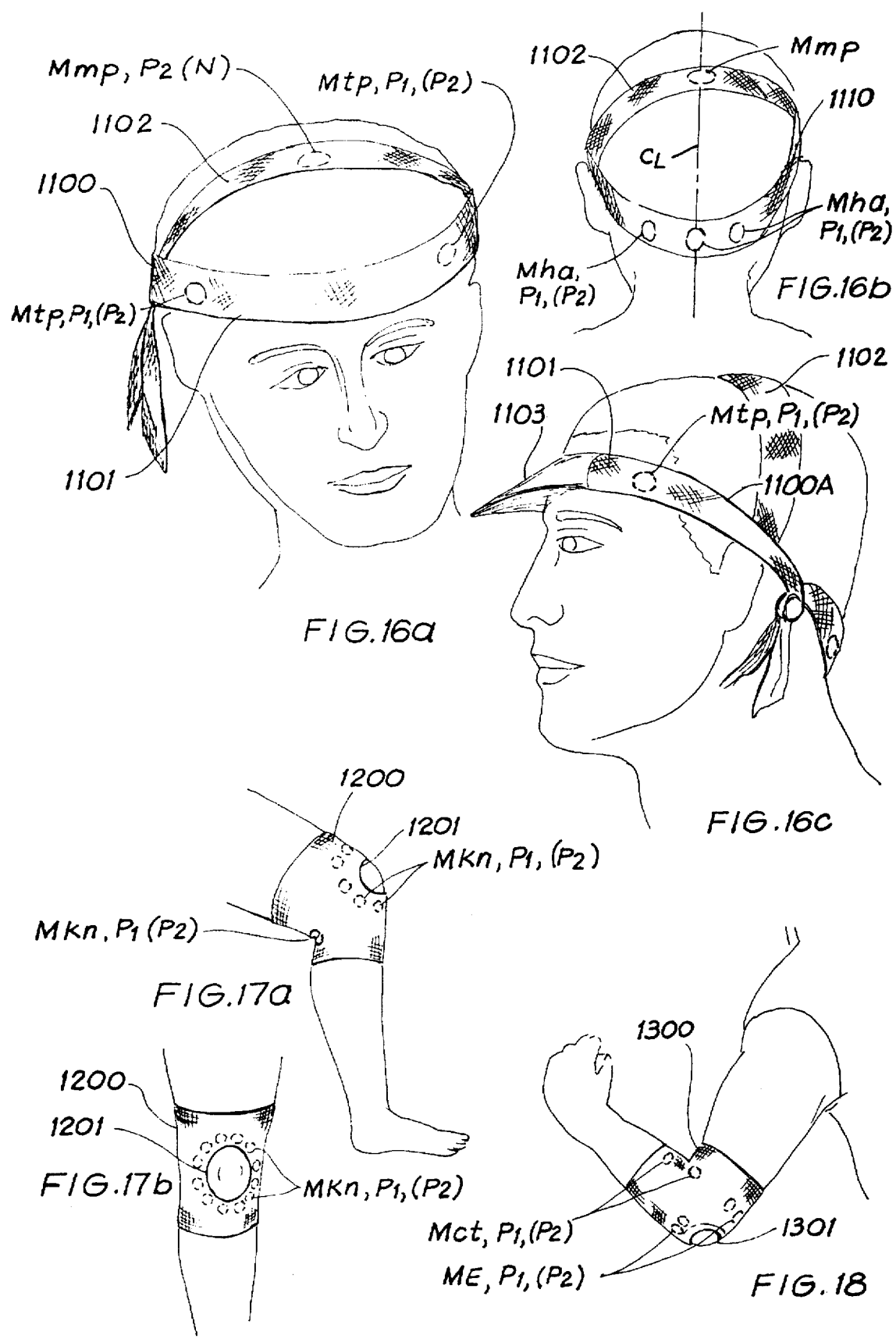

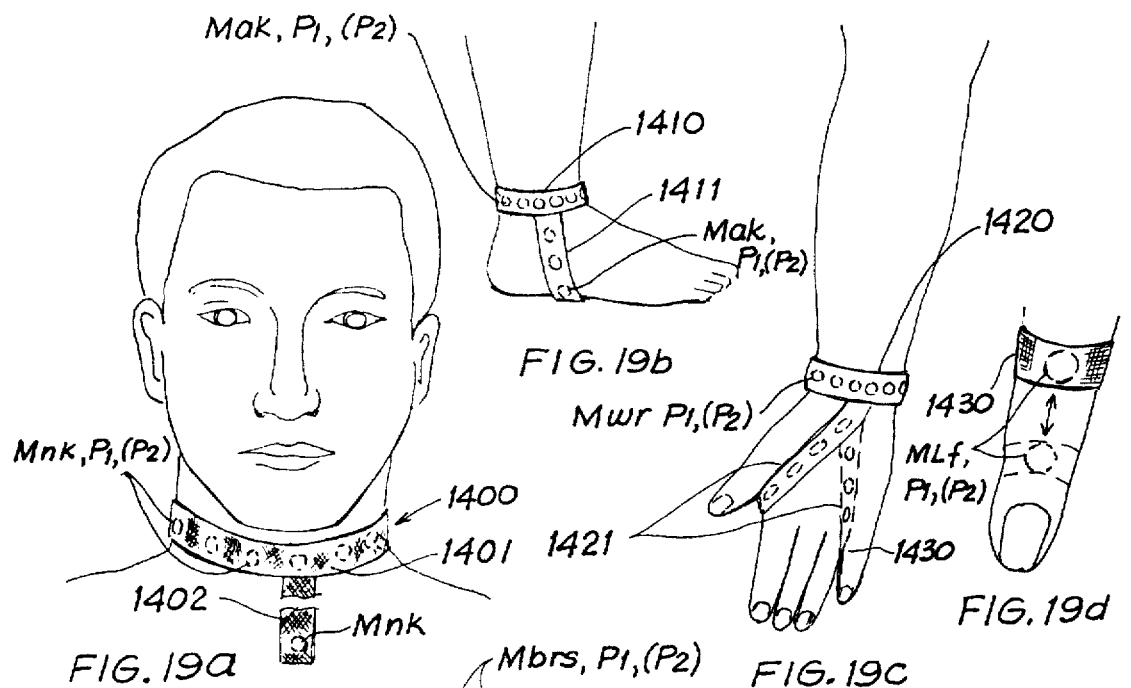
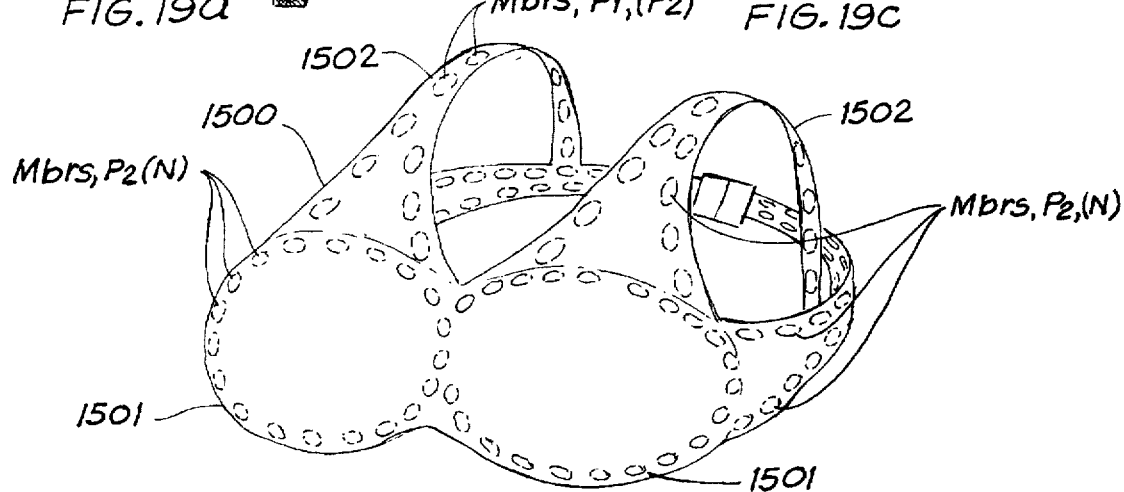
FIG. 20
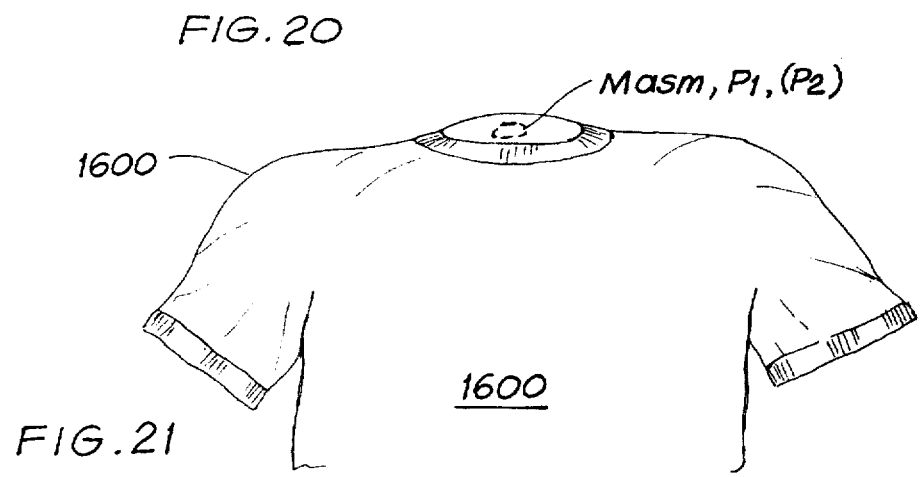
FIG. 21

ARTICLES OF HUMANWEAR MERCHANDISE HAVING MAGNETIC STRUCTURE FOR PRODUCING MAGNETIC HEALING EFFECTS

FIELD OF THE INVENTION

The present invention relates to merchandise worn by humans. More particularly, the present invention relates to merchandise worn by humans for therapeutic reasons. Even more particularly, the present inventions relates to merchandise having magnetic structure that is worn by humans for therapeutic trains.

BACKGROUND OF THE INVENTION

Acupuncture is an original Chinese practice of needle puncturing the body at specific points on the body to cure disease, or relieve pain. The specific points are well documented and known to practitioners in the art, and have been used in the related practice of shiatsu. Shiatsu pertains to the massage therapy applied with the fingers to those specific areas of the body used in acupuncture, also termed acupressure. Magnetic healing/therapy is another related practice that has utilized the same specific points on the body known to acupuncture and acupressure practitioners.

The magnetic therapy practice has caused the development of products with permanent magnets distributed on the products. For example, U.S. Pat. No. 4,509,219 teaches a sleeping mattress structure provided with permanent magnets each having a magnetic field strength of at least 850 gauss which are disposed on the mattress for maximum magnetic curing effect. U.S. Pat. No. 4,921,560 teaches a method for fixing the permanent magnets to bed covering. Merchandise worn by humans having magnetic structure has also been developed. For example, Japan Life Products 1992 Catalog, at page 10 and 11, shows belts, elbow and knee supporters, wrist and foot support massager provided with magnetic structure. Similarly, OMS Medical Supplies 1992-93 Catalog, at pages 59-67, shows humanwear merchandise provided with magnetic structure. The DMS merchandise includes head bands, vests, belts, wrist bands, supports for the elbows, arms, legs, knee and ankle, and also necklaces.

The apparent premise for the merchandise provided with the magnetic structure is to place a permanent magnet such that body cells are exposed to a low-level magnetic field emitted from the permanent magnets. The magnetic exposure is believed to assist stressed cells in restoring their correct balance of electrical charge for performing more efficiently, see undated article by Japan Life Products, entitled: "Spreading Good Sleep Around the World". The magnetic exposure when concentrated at the same specific points on the body known to acupuncture and acupressure practitioners is a developing therapeutic practice. The practitioner is limited by lack of variety in the merchandise provided with the magnetic structure to carry out the strategic magnetic exposure. The limitation has resulted in the practitioner having to use discrete permanent magnets secured to the particular body point to effect the magnetic exposure. The permanent magnets are commercially available in a variety of shapes and magnetic strengths, see for example OMS Medical Supplies 1992-93 Catalog, at pages 74-75. The user of the discrete permanent magnet has to generally tape the magnet onto the particular body point being treated. The taped magnets are not particularly fashionable, and are often times not the best means of securing the magnet to the body part, for example onto hair at the soft spot of the human head, or when several permanent magnets are required to produce the maximum magnetic exposure.

Therefore, a need is seen to exist for a larger variety of specialized merchandise provided with the magnetic structure that is worn by humans for magnetic exposure therapeutic reasons.

In particular, a need is seen to exist for merchandise in the form of torso-worn garments provided with the magnetic structure that corresponds to selected acupressure regions and points on the human torso for effecting therapeutic magnetic exposure when worn by a human user.

A particular need is seen to exist for merchandise in the form of gloves that have magnetic structure that corresponds to selected acupressure regions and points on the human hand for effecting therapeutic magnetic exposure when worn by a human user.

In general, a need is seen to exist for a larger variety of merchandise in the form of gear for the human head and body appendages that has magnetic structure that corresponds to selected acupressure regions and points on the human head and appendages for effecting therapeutic magnetic exposure when worn by a human user.

SUMMARY OF THE INVENTION

Accordingly, the primary object of the present invention is to provide a larger variety of specialized merchandise that is worn by humans for magnetic exposure therapeutic reasons.

A particular object of the present invention is to provide merchandise in the form of torso-worn garments provided with the magnetic structure that corresponds to selected acupressure regions and points on the human torso for affecting therapeutic magnetic exposure when worn by a human user.

Another particular object of the present invention is to provide merchandise in the form of gloves that have magnetic structure that corresponds to selected acupressure regions and points on the human hand for affecting therapeutic magnetic exposure when worn by a human user.

Yet another object of the present invention is to provide a larger variety of merchandise in the form of gear for the human head and body appendages that has magnetic structure that corresponds to selected acupressure regions and points on the human head and body appendages for affecting therapeutic magnetic exposure when worn by a human user.

The foregoing objects are accomplished by providing a variety of torso-worn garments, gear for the human head and body appendages that have magnetic structure that corresponds to selected acupressure regions and points on the human torso, head and body appendages for affecting therapeutic magnetic exposure when worn by a human user. In particular, the objects of the present invention are accomplished by: (1) providing several glove designs that incorporate magnetic structure that corresponds to shiatsu meridian lines on the human hands, and to particular acupressure points on the human hand for facilitating magnetic exposure to those regions and points of the hand, (2) providing torso-worn garments, including T-shirts, pants, briefs, and brassieres, that incorporate magnetic structure that corresponds to shiatsu meridian lines on the human body, and to particular acupressure points on the human body for facilitating magnetic exposure to those regions and points of the body, and (3) otherwise providing gear for the human head and body appendages, including a facemask, a visored-headband, footwear, ankle/foot band support, wrist/finger band support, neckband support (not necklaces), localized elbow and knee support bands, that has magnetic structure interdisposed with the primary structure of the gear and that corresponds to selected acupressure regions and points on the human head and body appendages for effecting therapeutic magnetic exposure when worn by a human user.

Therefore, to the accomplishments of the foregoing objects, the invention consists of the foregoing features hereinafter fully described and particularly pointed out in the claims, the accompanying drawings and the following disclosure describing in detail the invention, such drawings and disclosure illustrating the preferred embodiments in which the invention may be practiced.

BRIEF DESCRIPTION OF THE DRAWINGS

FIG. 12 shows human torso-worn garment merchandise in the form of a T-shirt having an embedded magnetic structural arrangement distributed in an orderly fashion throughout the body of the T-shirt, substantially as shown.

FIG. 13 shows humanwear garment merchandise in the form of pants having an embedded magnetic structural arrangement distributed in an orderly fashion throughout the body of the pants, substantially as shown.

FIG. 14 shows human torso-worn garment merchandise in the form of briefs having an embedded magnetic structural arrangement distributed in an orderly fashion throughout the body of the briefs.

FIG. 15 shows human appendagewear merchandise in the form of footwear having an embedded magnetic structural arrangement distributed in an orderly fashion throughout the body of the footwear.

FIG. 16a shows human headwear merchandise in the form of a headband/across-the-head band design having an embedded magnetic structural arrangement in the form of discrete permanent magnets having a first, or second, polarity positioned inwardly toward a user's head, substantially as shown, at the headband's side and cross member band portions.

FIG. 16b shows a rear view of the headwear merchandise illustrated in FIG. 16a showing additional discrete permanent magnets also having a first polarity positioned inwardly toward a user's head, spaced apart substantially as shown at the rear of the headband.

FIG. 16c shows a modified version of the headwear merchandise illustrated in FIGS. 16a and 16b wherein a visor is provided for purposes of encouraging outdoor use of the headgear.

FIGS. 17a and 17b show human appendagewear merchandise in the form of a knee band support having an embedded magnetic structural arrangement in the form of a plurality of circumferentially distributed permanent magnets strategically arranged about an opening in the knee cap portion of the support.

FIG. 18 shows human appendagewear merchandise in the form of an elbow band support having an embedded magnetic structural arrangement in the form of a plurality of permanent magnets strategically arranged about an opening in the elbow portion of the support.

FIG. 19a shows human appendagewear merchandise in the form of a neckband article having an embedded magnetic structural arrangement in the form of a plurality of circumferentially distributed permanent magnets embedded in a neck band member, and a suspended band member also provided with at least one permanent magnet, each permanent magnet having a same polarity positioned inwardly toward a user's neck.

FIG. 19b shows human appendagewear merchandise in the form of an ankle-to-foot support band having an embedded magnetic structural arrangement about the ankle and foot band members in the form of a plurality of permanent magnets each having a same polarity positioned inwardly toward a user's ankle and foot, substantially as shown.

FIG. 19c shows human appendagewear merchandise in the form of a wrist-to-hand support band having an embedded magnetic structural arrangement around the wrist and hand band in the form of a plurality of permanent magnets each having a same polarity positioned inwardly toward a user's wrist and hand, substantially as shown.

FIG. 19d shows human appendagewear merchandise in the form of an adjustable finger support band, as shown in FIG. 19c, having an embedded magnetic structural arrangement in the form of at least one permanent magnet having a first polarity positioned inwardly toward a user's finger, substantially as shown.

FIG. 20 shows human torso-worn garment merchandise in the form of a brassiere having an embedded magnetic structural arrangement in the form of a plurality of permanent magnets, each having a first polarity positioned inwardly around cup portions of the brassiere and along the outer edges of the straps, substantially as shown.

FIG. 21 shown human torso-worn garment merchandise in the form of a T-shirt having an embedded magnetic structural arrangement in the form of at least one strategically positioned permanent magnet having a first polarity positioned inwardly at the knap of the neck region of the T-shirt, substantially as shown.

DESCRIPTION OF THE PREFERRED EMBODIMENT

Figures 1, 2:
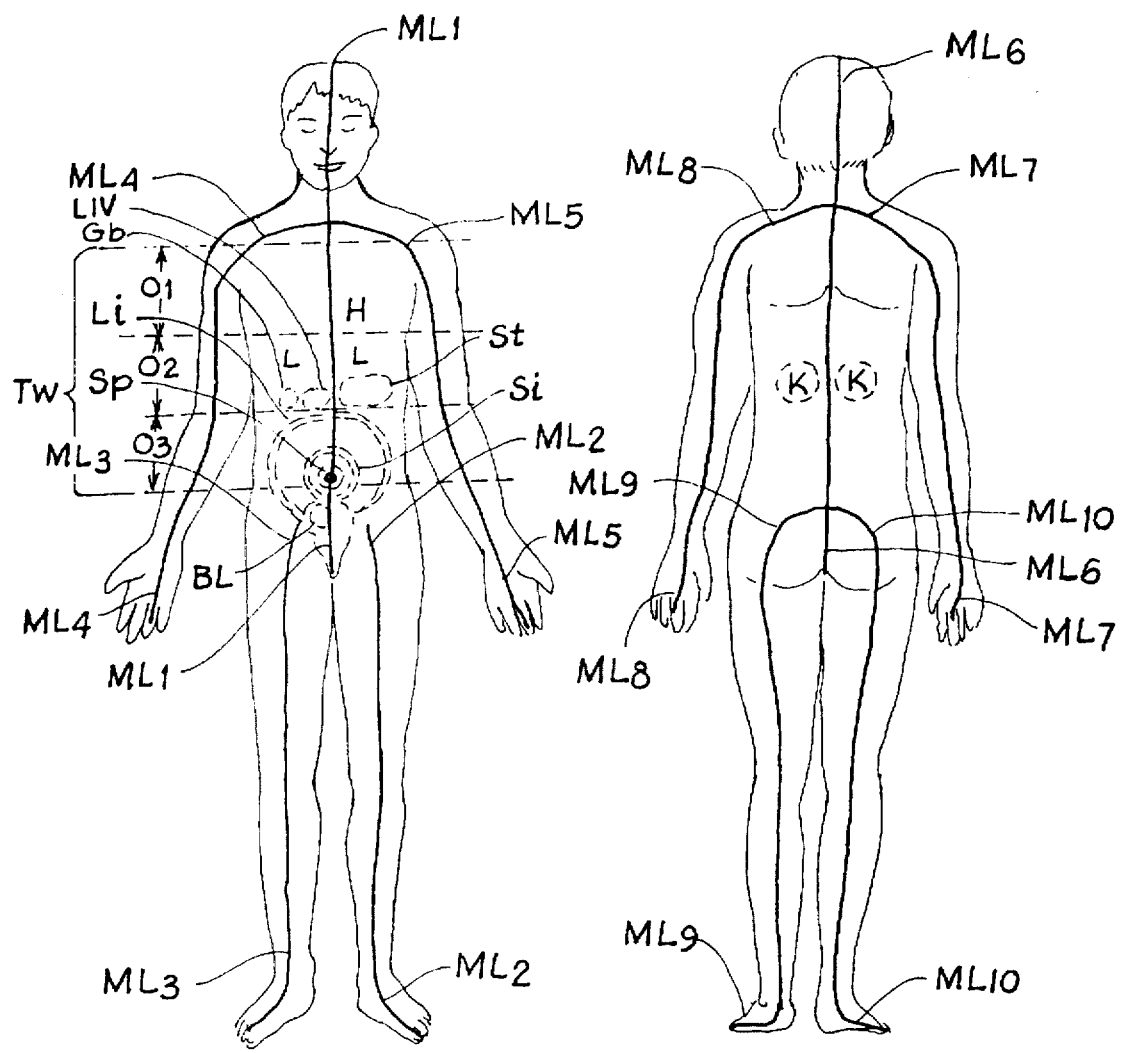
FIG. 1 shows a frontal view of a human body diagrammed to illustrate regions of the human anatomy, including body meridian lines, shiatsu body points that are the target for being magnetically exposed by the magnetic structure in the humanwear merchandise of the present invention.
FIG. 2 shows a backside view of a human body also diagrammed to illustrate regions of the human anatomy, including body meridian lines and shiatsu body points, that are the target for being magnetically exposed by the magnetic structure in the humanwear merchandise of the present invention.

FIG. 1 shows a frontal view of a human body diagrammed to illustrate shiatsu regions of the human anatomy. The diagram includes body meridian lines ML(1-5), shiatsu body points for the body region known as the triple warmer Tw, which includes organ regions 01 (heart H), 02 (liver Li, lungs L, stomach St) and 03 (large intestines Li, small intestines Si and spleen Sp) that are the target for being magnetically exposed or impacted by the magnetic structure in the humanwear merchandise of the present invention. FIG. 2 shows a backside view of a human body also diagrammed to illustrate shiatsu regions of the backside of the human anatomy, including body meridian lines ML (6-10) and shiatsu body points for the kidneys, that are the target for being magnetically exposed, or impacted by the magnetic structure in the humanwear merchandise of the present invention.

Figures 3, 5:
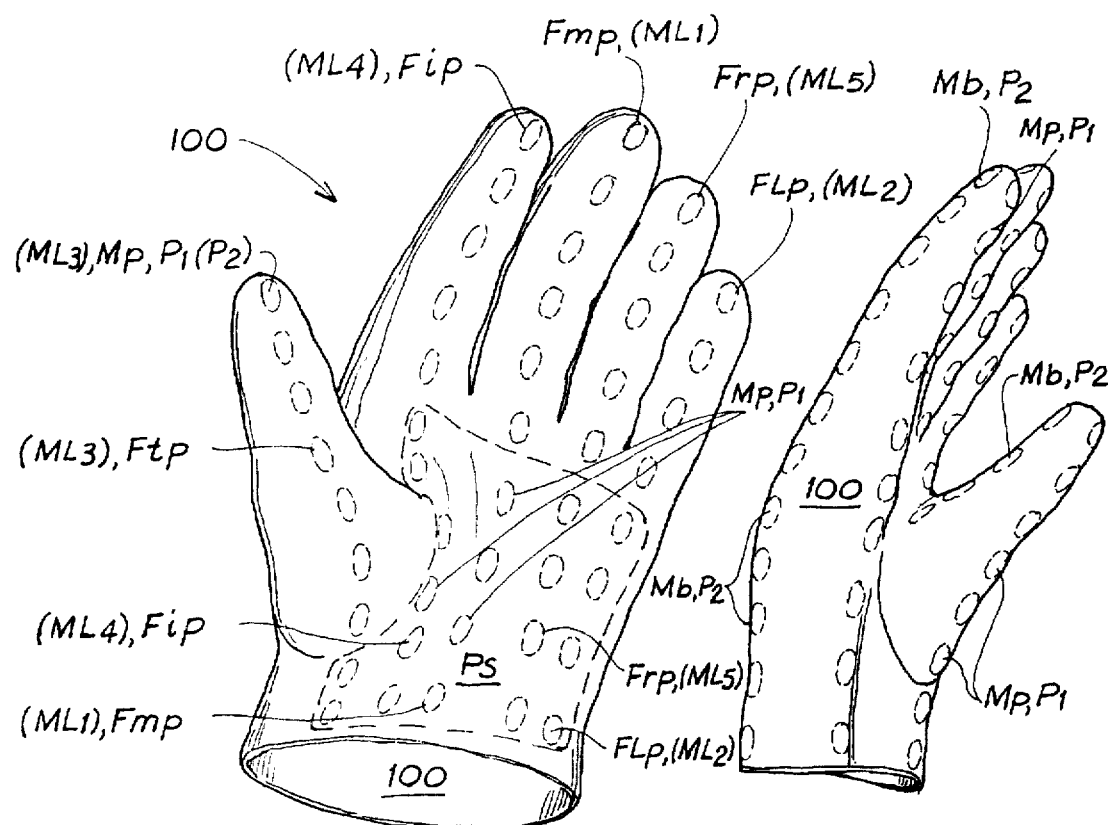
FIG. 3 shows a palm side view of a general purpose glove provided with embedded magnetic structure in the form of discrete permanent magnets of a first polarity arranged to extend from the distal end of each of the glove's digits towards the glove's wrist end.
FIG. 5 is a side view of the general purpose glove illustrated in FIGS. 3 and 4 showing the preferred side-by-side arrangement of the permanent magnets embedded in the glove's fabric, see also FIG. 24.
Figure 4:
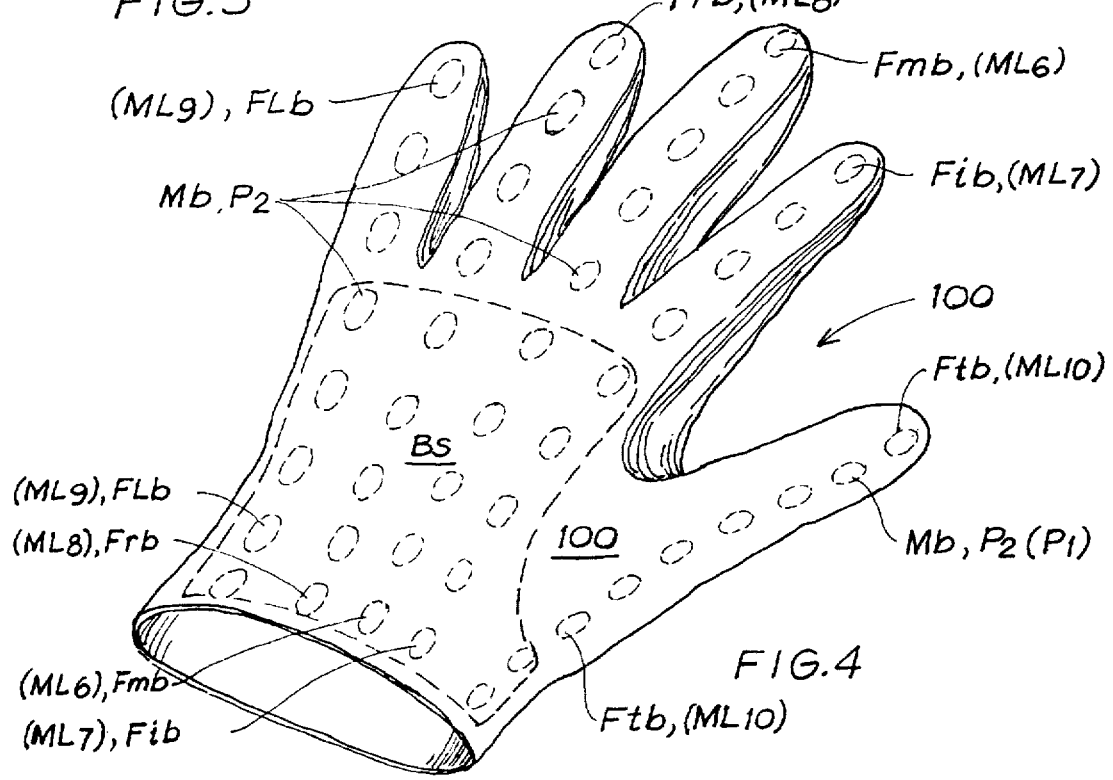
FIG. 4 shows a back side view of a general purpose glove provided with embedded magnetic structure in the form of discrete permanent magnets of a second polarity arranged to extend from the distal end of each of the glove's digits towards the glove's wrist end.
Figure 24:
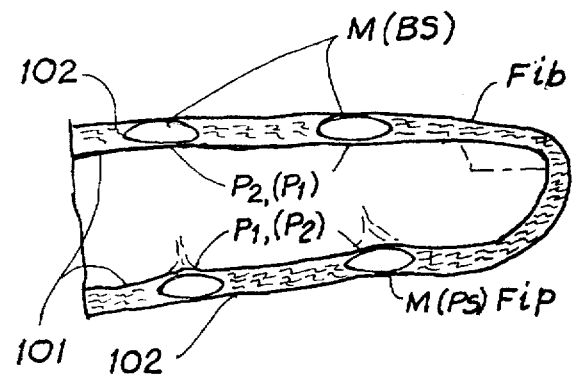
FIG. 24 shows a cross-section of finger portion of a glove article adapted with a magnetic structure in accordance with the permanent magnet's pole orientation as illustrated in FIG. 23.

FIG. 3 shows a palm side view of a general purpose glove 100 provided with embedded magnetic structure in the form of a plurality of discrete permanent magnets Mp of a first polarity P1, or alternatively a second polarity P2, arranged to extend serially from the distal end of each of the glove's digits towards the glove's wrist end, denoted by the letters Ftp (thumb-wrist), Fip (index finger-wrist), Fmp (middle finger-wrist), Frp (ring finger-wrist), and FLp (little finger-wrist). The serial arrangement of magnets Mp on each digit follows a centerline of each digit and are spaced apart on the pale and wrist area of the glove. The polarity, P1 (P2), of permanent magnets Mp is oriented inwardly toward the inside of the glove, substantially as illustrated in FIG. 24. Similarly, FIG. 4 shows a back side view of glove 100 also provided with embedded magnetic structure in the form of discrete permanent magnets Mb of a second polarity P2, or alternatively a second polarity P1, arranged to extend from the distal nail-end of each of the glove's digits towards the glove's wrist end, denoted by the letters Ftb (thumb-wrist), Fib (index finger-wrist), Fmb (middle finger-wrist), Frb (ring finger-wrist), and FLb (little finger-wrist), Glove 100 is preferably constructed having an inner layer 101 and an outer layer toe for adhesively containing each discrete magnet Mp. The permanent magnets each have a magnetic field strength of at least 800 gauss and are of the type commercially available from Lhasa Medical Supplies, Inc., Accord, Mass. USA. The magnetic field that is produced by the plurality of magnets Mp, Mb is directed at strategic points on the wearer's hand, which points relate to the human body according to shiatsu practice. By example, glove 100 represent a left hand glove where the magnets along the middle finger to the wrist portion, (palm side PS and backside BS), of the glove relate to the body regions along meridian line (ML1, ML6), beginning at the head and ending at the groin. Similarly, the magnets along the ring finger to the wrist portion of the glove relate to the body regions along meridian line (ML5, ML8), beginning at the left hand and ending at the left shoulder, the magnets along the little finger to the wrist portion of the glove relate to the body regions along meridian line (ML2, ML9), beginning at the left foot and ending at the left hip, the magnets along the index finger to the wrist portion of the glove relate to the body regions along meridian line (ML4, ML7), beginning at the right hand and ending at the right shoulder, and the magnets along on the thumb to the wrist portion of the glove relate to the body regions along meridian line (ML3, ML10), beginning at the right foot and ending at the right hip. Upon the glove 100 being worn on a human hand, the underlying regions of the hand are magnetically exposed by the permanent magnets Mp, Mb. The exposure is believed to therapeutically impact the human body parts along the meridian line (ML1-ML10). FIG. 5 shows a side view of the general purpose glove illustrated in FIGS. 3 and 4 showing the preferred side-by-side arrangement of the permanent magnets embedded in the glove's fabric, see also FIG. 24.

Figures 6, 7:
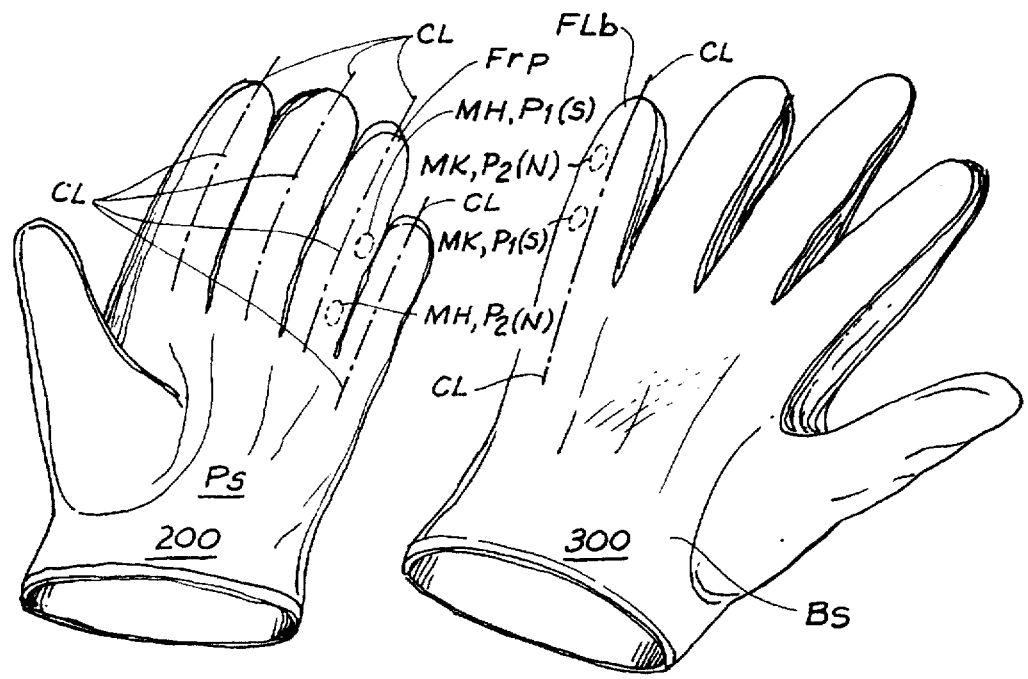
FIG. 6 shows a palm side view of a left-hand, heart-impacting specialty glove provided with embedded magnetic structure in the form of two discrete permanent magnets having opposite polarities positioned inwardly on the glove's ring finger, substantially as shown at the glove's finger joints.
FIG. 7 shows a back side view of a left-hand, kidney-impacting specialty glove provided with embedded magnetic structure in the form of two discrete permanent magnets having opposite polarities positioned inwardly on the glove's little finger, substantially as shown at the glove's finger joints.

FIG. 6 shone a palm side view of a left-hand, heart-impacting specialty glove 200 provided with strategically embedded magnetic structure in the form of two discrete permanent magnets MH having opposite polarities P1 (S), P2 (N), positioned inwardly and along a centerline CL of the glove's ring finger Frp at the glove's finger joints. Upon the glove 200 being worn on a human hand, the underlying joint regions of the ring finger are magnetically exposed by the permanent magnets MH. The exposure is believed to therapeutically impact the heart H.

FIG. 7 shows a back side view of a left-hand, kidney-impacting specialty glove 300 provided with embedded magnetic structure in the form of two discrete permanent magnets MK having opposite polarities P1 (S), P2 (N) positioned inwardly and to the left of the centerline of the glove's little finger FLb, at the glove's finger joints. Upon the glove 300 being worn on a human hand, the underlying joint regions of the little finger are magnetically exposed by the permanent magnets MK. The exposure is believed to therapeutically impact the kidneys K.

Figures 8, 9:
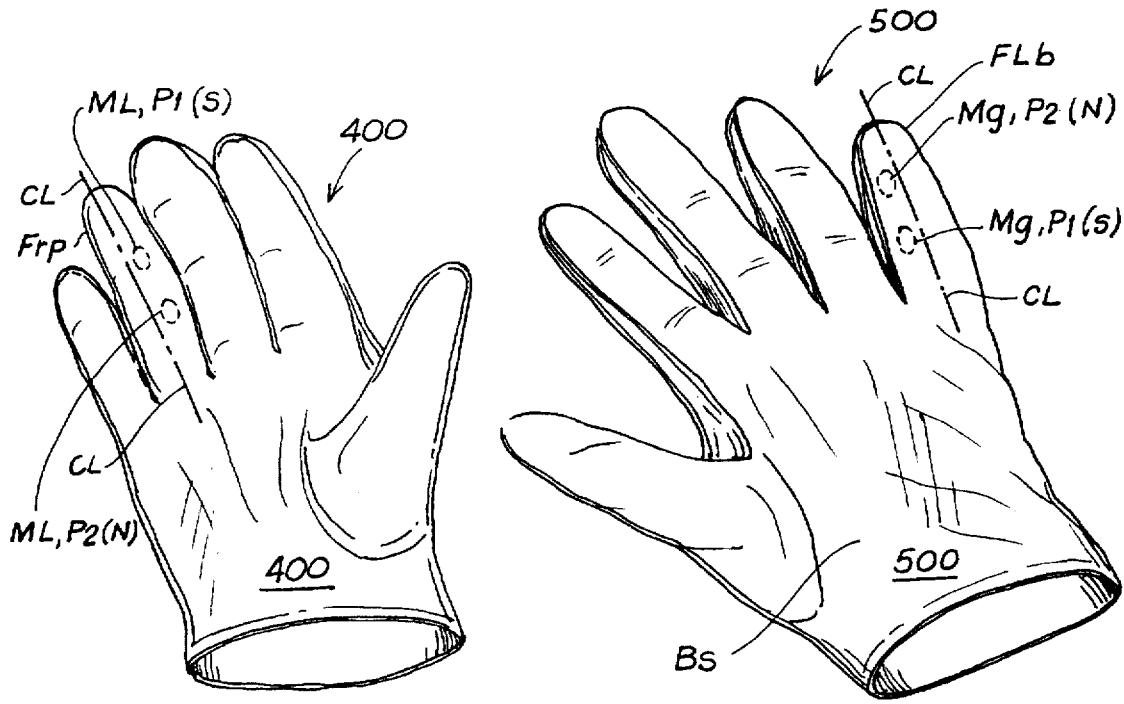
FIG. 8 shows a palm side view of a right-hand, lung-impacting specialty glove provided with embedded magnetic structure in the form of two discrete permanent magnets having opposite polarities positioned inwardly on the glove's ring finger, substantially as shown at the glove's finger joints.
FIG. 9 shows a back side view of a right-hand, gall bladder-impacting specialty glove provided with embedded magnetic structure in the form of two discrete permanent magnets having opposite polarities positioned inwardly on the glove's little finger, substantially as shown at the glove's finger joints.

FIG. 8 shows a palm side view of a right-hand, lung-impacting specialty glove 400 provided with embedded magnetic structure in the form of two discrete permanent magnets ML having opposite polarities P1 (S), P2 (N) positioned inwardly and to the right of the centerline CL on the glove's ring finger Frp, at the glove's finger joints. Upon the glove 400 being worn on a human hand, the underlying joint regions of the ring finger are magnetically exposed by the permanent magnets ML. The exposure is believed to therapeutically impact the lungs L.

FIG. 9 shows a back side view of a right-hand, gall bladder-impacting specialty glove 500 provided with embedded magnetic structure in the form of two discrete permanent magnets Mg having opposite polarities P1 (S), P2 (N), positioned inwardly and to the left of centerline CL on the glove's little finger FLb, at the glove's finger joints. Upon the glove 500 being worn on a human hand, the underlying joint regions of the little finger are magnetically exposed by the permanent magnets Mg. The exposure is believed to therapeutically impact the gall bladder Gb.

Figures 10A, 10B:
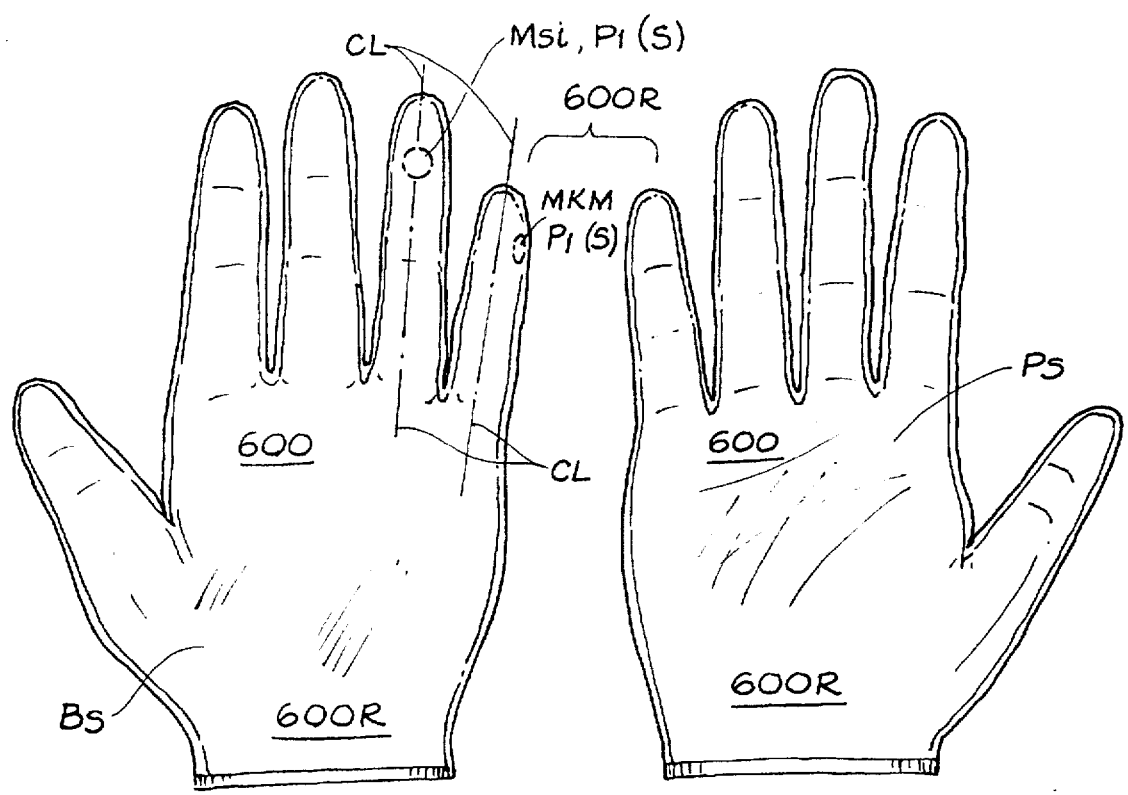
FIG. 10a shows a back side view of a right-hand glove member, of a specialty power glove set, provided with embedded magnetic structure in the form of a first discrete permanent magnet having a first polarity positioned inwardly on the glove's little finger, and a second discrete permanent magnet having the same first polarity positioned inwardly on the glove's ring finger, substantially as shown on the glove's fingers.
FIG. 10b shows a palm side view of the right-hand glove member illustrated in FIG. 10a showing the palm side as being void of embedded magnetic structure.
Figures 11A, 11B:
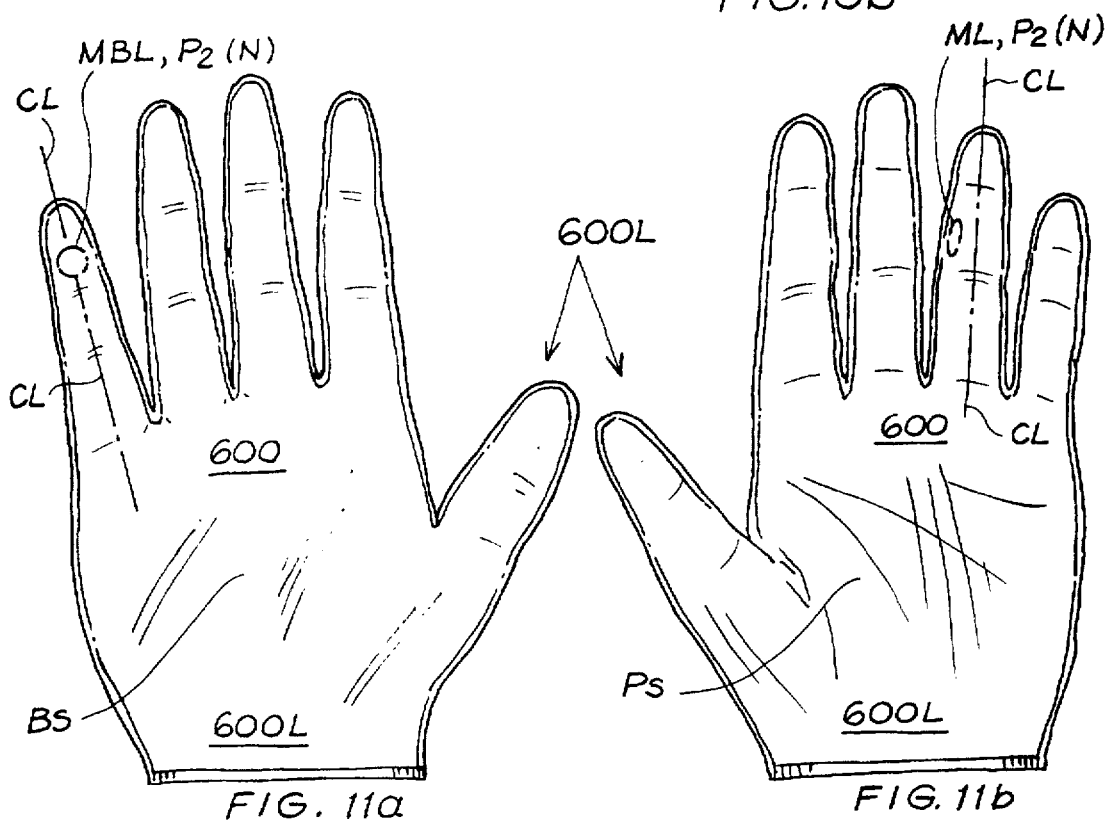
FIG. 11a shown a back side view of a left-hand glove member, of a specialty power glove set, provided with embedded magnetic structure in the form of a sole discrete permanent magnet having a second polarity positioned inwardly on the glove's little finger, substantially as shown on the glove's finger.
FIG. 11b shows a palm side view of the left-hand glove member illustrated in FIG. 11a provided with embedded magnetic structure in the form of a sole discrete permanent magnet having a second polarity positioned inwardly on the glove's ring finger, substantially as shown on the glove's finger.

FIG. 10a shows a back side Bs of a right-hand glove member 600R, of a specialty power glove set 600. Glove member 600R is provided with embedded magnetic structure in the form of a first discrete permanent magnet MKM having a first polarity P1 (S) positioned inwardly and to the right of centerline Cl on the glove's little finger, above the distal joint, and a second discrete permanent magnet MSi having the same first polarity P1 (S) positioned inwardly on the glove's ring finger, on the centerline of, the glove's ring finger above the distal joint. FIG. 10b shows a palm side Ps of right-hand glove ember showing the palm side as being void of embedded magnetic structure. FIG. 11a shows a back side Bs of a left-hand glove member 600L, of specialty power glove set 600, provided with embedded magnetic structure in the form of a sole discrete permanent magnet MBL having a second polarity P2 (N) positioned inwardly on the glove's little finger, on the centerline CL, and above the distal joint and below a wearer's nail, substantially as shown on the glove's little finger. FIG. 11b shown a palm side Ps of left-hand glove member 600L, provided with embedded magnetic structure in the form of a sole discrete permanent magnet ML having a second polarity P2 (N) positioned inwardly and to the left of the centerline CL between the two joints on the glove's ring finger, substantially as shown on the glove's finger. Upon the glove 600L being worn on a human hand, the underlying regions of the little finger and ring finger are magnetically exposed by the permanent magnets MBL,ML, respectively. The exposure is believed to therapeutically impact the bladder and lungs, respectively.

The glove covering of gloves 200, 300, 400, 500 and 600 is preferably, constructed similar to glove 100, wherein an inner covering layer 101 and an outer covering layer 102 are provided for adhesively containing each respective discrete magnet on gloves 200, 300, 400, 500 and 600, see generally FIG. 24. Similarly, the permanent magnets, on gloves 200, 300, 400, 500 and 600, each have a magnetic field strength of at least 800 gauss and are of the type commercially available from Lhasa Medical Supplies, Inc., Accord, Mass. USA.

FIG. 12 shows human torso-worn garment merchandise in the form of a T-shirt 700 having an embedded magnetic structural arrangement Mt distributed evenly, as depicted by spacing d, in an orderly fashion throughout the body of the T-shirt, including short sleeves 701, or alternatively on long sleeves 702, substantially as shown. The inwardly directed polarity of magnets Mt is preferably all the same polarity, i.e., all P1, or all P2. Upon T-shirt being worn by a human, the underlying regions of the upper torso and arms are magnetically exposed by the permanent magnets Mt. The exposure is believed to therapeutically impact the upper torso and arms.

FIG. 13 shows human torso-worn garment merchandise in the form of leotard-type pants 800 having an embedded magnetic structural arrangement MLt distributed in an orderly fashion throughout the lower torso and legs of the pants, substantially as shown. The inwardly directed polarity of magnets MLt is preferably all the same polarity, i.e., all P1, or all P2. Upon pants 800 being worn by a human, the underlying regions of the lower torso and legs are magnetically exposed by the permanent magnets MLt. The exposure is believed to therapeutically impact the lower torso and legs.

FIG. 14 shows human torso-worn garment merchandise in the form of briefs 900 having an embedded magnetic structural arrangement Mbr distributed in an orderly fashion throughout the body of the briefs, including the crotch portion 901, substantially as shown. The inwardly directed polarity of magnets Mbr is preferably all the same polarity, i.e., all P1, or all P2. Upon briefs 800 being worn by a human, the underlying regions of the wearer's lower torso and crotch are magnetically exposed by the permanent magnets Mbr. The exposure is believed to therapeutically impact the wearer's lower torso and crotch.

FIG. 15 shows human appendagewear merchandise in the form of sock-like footwear 1000 having an embedded magnetic structural arrangement Ms distributed in an orderly fashion throughout the lower body of the sock-like footwear. The sole portion 1001 may also be provided with magnet structure Ms. The inwardly directed polarity of magnets Ms is preferably all the same polarity, i.e., all P1, or all P2. Upon footwear 1000 being worn by a human, the underlying regions of the wearer's lower foot, (and/or optionally the wearer's sole) are magnetically exposed by the permanent magnets Ms. The exposure is believed to therapeutically impact the wearer's foot.

FIG. 20 shows human torso-worn garment merchandise in the form of a brassiere 1500 having an embedded magnetic structural arrangement in the form of a plurality of permanent magnets Mbrs. Preferably, each magnet is oriented having the north polarity P2 (N) positioned inwardly around cup portions 1501 and having either polarity P1, or P2 oriented inwardly along the outer edges of the straps 1502, substantially as shown. Upon brassiere 1500 being worn by a human, the underlying regions around the wearer's breasts and strapped regions are magnetically exposed by the permanent magnets Ms. The exposure is believed to therapeutically impact the wearer's breasts and strapped regions.

FIG. 21 shows human torso-worn garment merchandise in the form of a T-shirt 1600 having an embedded magnetic structural arrangement in the form of at least one strategically positioned permanent magnet Masm. The inwardly directed polarity of magnet Masm may be either P1, or P2, see FIG. 23. The strategic placement of magnet Masm is at the knap of the neck region of the T-shirt, substantially as shown. Upon T-shirt 1600 being worn by a human, the underlying region around the wearer's lower neck, substantially at vertebrae number 1, is magnetically exposed by the permanent magnets Masm. The exposure is believed to therapeutically impact the wearer's bronchial region and to minimize asthma.

The humanwear merchandise 700, 800, 900, 1000, 1500 and 1600 is preferably, constructed by permanently adhering the respective magnets on the inside portion of the fabric from which the respective merchandise is made from. By example, upon producing the merchandise 700, 800, 900, 1000, 1600, the magnets may be provided on a roll in the form of ribbon-like strips having an adhesive backing, which backing would be removed upon applying the adhesive-carrying magnets to the inside portion of the fabric. The bond between each magnet and the fabric should be durable to withstand being multi-washed and multi-worn. The desired interior-directed polarity of the magnets, i.e., north or south, should be determined before being bonded. The body side of the magnet should be cladded to minimize skin irritation. The cladding should not block the magnetic emission when worn. A double layer fabric construction, similar to the structure proposed for gloves 100–600 is acceptable, however, care should be taken that the interior fabric layer does not block the magnetic emission from the embedded magnets.

FIG. 16a shows human headwear merchandise in the form of a combination-type of headgear 1100. Headgear 1100 includes a traditional headband 1101 in combination with an across-the-head band member 1108. Headgear 1100 is formed having a strategic embedded magnetic structural arrangement in the form of discrete permanent magnets Mtp positioned on band member 1101 for contacting a wearer's temporal region, discrete magnets Mmp positioned on band member 1102 for contacting a wearer's soft spot, and discrete magnets Mha positioned at rear band portion 1110, (see FIG. 16b), for contacting a wearer's uppermost vertebrae region at the base of the skull. The inwardly directed polarity of magnets Mtp and Mha may be either PI, or P2, see FIG. 23, while the inwardly directed polarity of magnet Mmp is preferably P2 (N). FIG. 16c shows visored headgear 1100A which is a modified version of headgear 1100. Headgear 1100A is adapted with a visor member 1103 for purposes of encouraging outdoor use of the magnetic structured headgear. Upon headgear 1100, 1100A being worn by a human, the underlying temporal region, the top of head region and the back base of the skull region, are magnetically exposed by the permanent magnets Mtp, Mmp and Mha. The magnetic exposure to those regions is believed to therapeutically impact the wearer's memory abilities, relieve headaches and relieve tension.

FIGS. 17a and 17b show human appendagewear merchandise in the form of a knee band support 1200 having an embedded magnetic structural arrangement in the form of a plurality of circumferentially distributed permanent magnets Mkn strategically arranged about an opening 1201 in the knee cap portion of the support. Opening 1201 helps magnets Mkn to remain located around the knee cap while being worn by a user. The inwardly directed polarity of magnet Mkn may be either P1, or P2, see FIG. 23, Upon support 1200 being worn by a human, the underlying region around the wearer's knee cap is magnetically exposed by the permanent magnets Mkn. The magnetic exposure around the knee cap regions is believed to therapeutically impact the knee.

FIG. 18 shows human appendagewear merchandise in the form of an elbow band support 1300 having an embedded magnetic structural arrangement in the form of a plurality of permanent magnets ME strategically arranged about an opening 1301 in the elbow portion of the support, and a pair of strategically positioned magnets Mct positioned at upper forearm substantially as shown. Opening 1301 helps magnets ME to remain located around the elbow while being worn by a user. The inwardly directed polarity of magnets ME and Mct may be either P1, or P2, see FIG. 23. Upon support 1300 being worn by a human, the underlying region around the wearer's elbow and the upper arm region are magnetically exposed by the permanent magnets ME and Mct. The magnetic exposure around the knee cap and upper arm regions is believed to therapeutically impact the elbow and minimize carpal tunnel ailments.

FIG. 19a shows human appendagewear merchandise in the form of a neckband 1400 having an embedded magnetic structural arrangement in the form of a plurality of circumferentially distributed permanent magnets Mnk embedded in a neck band member 1401, and a suspended band member 1402. The inwardly directed polarity of magnets Mnk may be either P1, or P2, see FIG. 23. Upon neckband 1400 being worn by a human, the underlying region around the wearer's neck and upper sternum regions are magnetically exposed by the permanent magnets Mnk. The magnetic exposure around the neck and upper sternum regions is believed to therapeutically impact the neck and sternum.

FIG. 19b shows human appendagewear merchandise in the form of an ankle-to-foot support band 1410/1411. Support band 1410/1411 includes an embedded magnetic structural arrangement about the ankle and foot band members in the form of a plurality of permanent magnets Mak inlaid within the band's fabric. The inwardly directed polarity of magnets Mak may be either P1, or P2, see FIG. 23. Upon support band 1410/1411 being worn by a human, the underlying region around the wearer's ankle and foot regions are magnetically exposed by the permanent magnets Mak. The magnetic exposure around the ankle and foot regions is believed to therapeutically impact the wearer's ankle and foot.

FIG. 19c shows human appendagewear merchandise in the form of a wrist-to-hand support band 1410/1411. Support band 1420/1421 includes an embedded magnetic structural arrangement around the wrist and hand band members in the form of a plurality of permanent magnets Mwr inlaid within the band's fabric. FIG. 19c and FIG. 19d also show human appendagewear merchandise in the form of an adjustable finger band 1430. Finger band 1430 is preferably formed from an elastic band material, commonly used in support bands to facilitate adjustment, but is further adapted to include an embedded magnetic structural arrangement in the form of at least one permanent magnet MLf inlaid within the band's fabric. The inwardly directed polarity of magnets Mwr and MLf may be either P1, or P2, see FIG. 23. Upon support band 1420/1421 and finger band 1430 being worn by a human, the underlying region around the wearer's wrist, hand and finger regions are magnetically exposed by the permanent magnets Mwr and MLf. The magnetic exposure around the wrist, hand and finger regions is believed to therapeutically impact the wearer's wrist, hand and finger.

Human appendagewear merchandise 1100, 1100A, 1200, 1300, 1400, 1410/1411, 1420/1421 and 1430 are preferably formed from an elastic band material, commonly used in support bands to facilitate a comfortable compressed state around the appendage wearing the support band. The embedded characteristic of the magnets on appendagewear merchandise is preferably achieved by adhesively retaining the magnets within a double layering of the band material, similar to the construction preferred for the glove merchandise, generally illustrated at FIG. 24. The permanent magnets used on the appendagewear merchandise each have a magnetic field strength of at least 800 gauss and are of the type commercially available from Lhasa Medical Supplies, Inc., Accord, Mass. USA.

Figure 22:
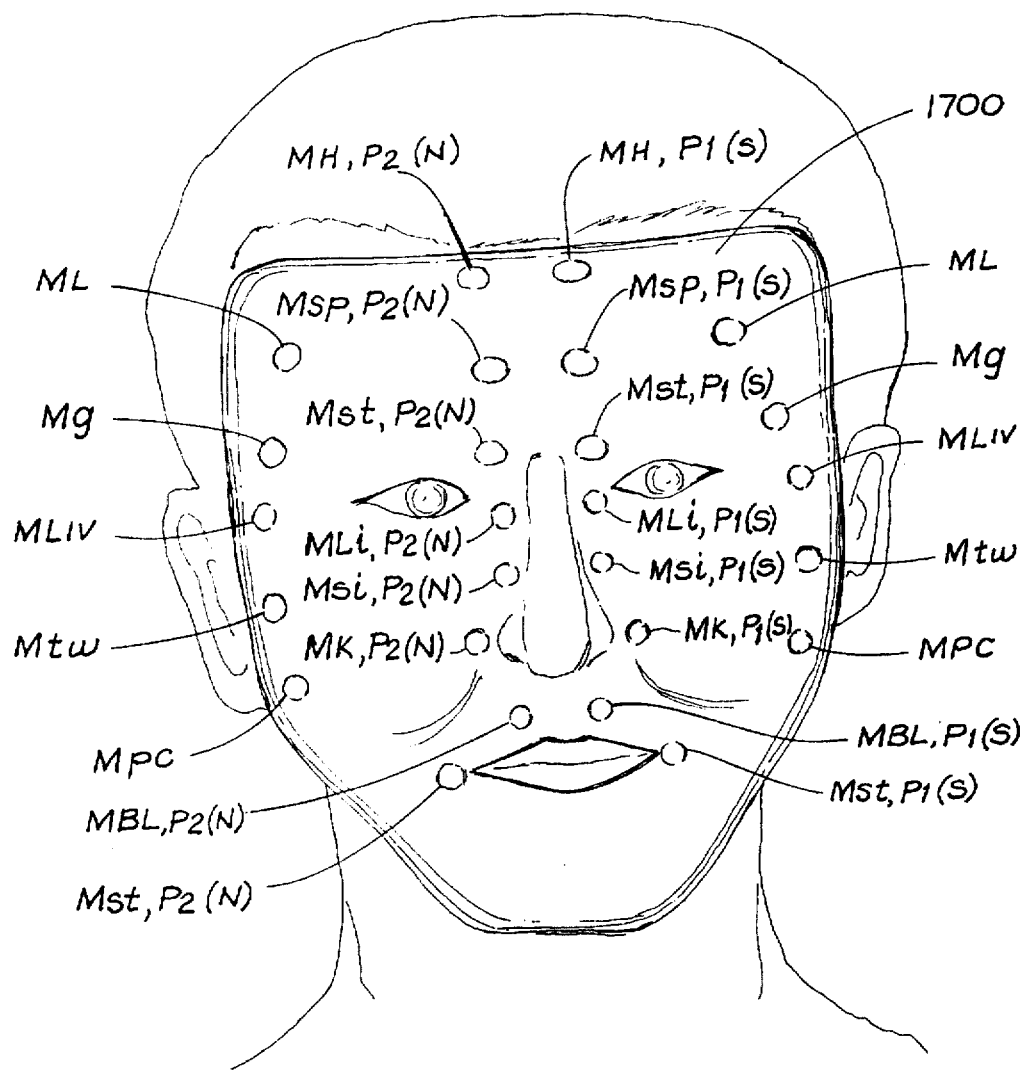
FIG. 22 shown human headwear merchandise in the form of a face mask having an embedded magnetic structural arrangement in the form of a plurality of symmetrically arranged permanent magnets, each symmetrical pair of magnets having opposite polarities positioned inwardly towards a user's face, substantially as shown.

Additional human headwear merchandise is shown at FIG. 22 in the form of a face mask 1700. Face mask 1700 is shown to include an embedded magnetic structural arrangement in the form of a plurality of symmetrically arranged permanent magnets Mst, MBL, Mpc, Mtw, Mliv, Mg, ML, MH, Msp, MLi, Msi and MK. Each symmetrical pair of magnets is inwardly directed such that opposite polarities P1, P2 contact a wearer's face, preferably such that polarity P2(N) contacts the left side of the wearer's face and polarity P1 (S) contacts the right side of the wearer's face. Upon face mask 1700 being worn by a human, the underlying illustrated facial points on the wearer's face are magnetically exposed by the permanent magnets Mst, MBL, Mpc, Mtw, Mliv, Mg, ML, MH, Msp, MLi, Msi and MK. The magnetic exposure by the magnets at the respective facial points is believed to therapeutically impact the wearer's stomach st, bladder BL, pericardium region pc, the triple warmer regions tw, the liver Liv, the gall bladder Gb, the lungs L, the heart H, the spleen sp, the large intestines Li, the small intestines si and kidneys K. As with the other humanwear merchandise of the present invention the magnets utilized in face mask 1700 each have a magnetic field strength of at least 800 gauss and are of the type commercially available from Lhasa Medical Supplies, Inc., Accord, Mass. USA.

Figure 23:
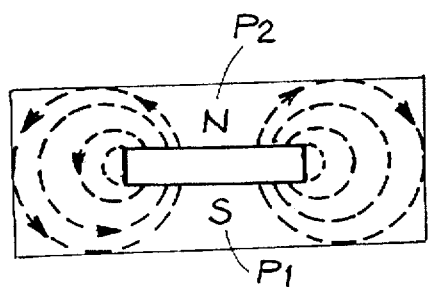
FIG. 23 shows a permanent magnet's pole orientation as utilized in the humanwear merchandise of the present invention.

As previously discussed, FIG. 23 shows a permanent magnet's pole orientation as utilized in the humanwear merchandise of the present invention. The magnets are preferably disk shaped and are substantially thin, typically (0.3 to 2.0) inches in diameter and (0.05 to 0.5) inches in thickness. The polarity N is the same as the earth's north pole and the polarity S is the same as the earth's south pole. Accordingly, the magnetic attraction is from north to south.

Securing the magnets to the material requires an adhesive treatment having high permanent bonding characteristics. A layered securement is preferred, as generally illustrated by layers 101, 102 in FIG. 24 for the glove merchandise of the present invention. Specifically, FIG. 24 shows a crosssection of an index finger portions Fib and Fip of the glove article shown in FIG. 5.

The merchandise of the present invention is to be considered investigation, and as such no prescription or medical claims are intended by the above suggested therapeutic uses on the human body.

Therefore, while the present invention has been shown and described herein in what is believed to be the most practical and preferred embodiments, it is recognized that departures can be made therefrom within the scope of the invention, which scope is therefore not to be limited to the details disclosed herein but is to be accorded the full scope of the claims so as to embrace any and all equivalent apparatus.

We claim:

1. An article of merchandise for human wear, said article comprising:

a glove member, said glove member being manufactured from at least one layer of covering material; and a permanent magnet structural arrangement comprising at least one permanent magnet attached to said covering material, said permanent magnet member having a substantially thin structure and being magnetically oriented such that a preselected first polarity is directed to the interior of said glove member for contacting and exposing a human wearer to a magnetic field associated with said permanent magnet, at least one of said permanent magnets positioned to contact a back of a hand of a human wearer.

2. An article of merchandise for human wear as described in claim 1, wherein:

said permanent magnet arrangement comprises a plurality of discrete permanent magnets arranged to extend from a distal end of a palm side and back side of each of said glove's digits towards a glove's wrist end portion on both palm and back side.

3. An article of merchandise for human wear as described in claim 1, wherein:

said glove member comprises a left-hand glove member, said left-hand glove member being provided with a magnetic structure in the form of two discrete permanent magnets having opposite first and second polarities oriented inwardly to the interior of a palm side of said left-hand glove member's ring finger.

4. An article of merchandise for human wear as described in claim 1, wherein:

said glove member comprises a left-hand glove member, said left-hand glove member being provided with a magnetic structure in the form of two discrete permanent magnets having opposite first and second polarities oriented inwardly to the interior of a back side of said left-hand glove member's little finger.

5. An article of merchandise for human wear as described in claim 1, wherein:

said glove member comprises a right-hand glove member, said right-hand glove member being provided with a magnetic structure in the form of two discrete permanent magnets having opposite first and second polarities oriented inwardly to the interior of a palm side of said right-hand glove member's ring finger.

6. An article of merchandise for human wear as described in claim 1, wherein:

said glove member comprises a right-hand glove member, said right-hand glove member being provided with a magnetic structure in the form of two discrete permanent magnets having opposite first and second polarities oriented inwardly to the interior of a back side of said right-hand glove member's little finger.

7. An article of merchandise for human wear as described in claim 1, wherein:

said article of merchandise comprises a left-hand glove member and a right-hand glove member of a glove set, said right-hand glove member being provided with embedded magnetic structure in the form of a first discrete permanent magnet having a first polarity oriented inwardly to an interior of a back side of said right-hand glove member's little finger, and a second discrete permanent magnet having said first polarity oriented inwardly to an interior of a back side of said right-hand glove member's ring finger; and said left-hand glove member being provided with embedded magnetic structure in the form of a sole discrete permanent magnet having a second polarity oriented inwardly to an interior of a back side of said left-hand glove member's little finger, and a second discrete permanent magnet having said second polarity oriented inwardly to an interior of a palm side of said left-hand glove member's ring finger.

8. A therapeutic apparatus comprising:
a) a glove member adapted to fit over a patient's hand; and,
b) at least two permanent magnets, each of said at least two permanent magnets,
1) having a substantially thin structure and being circular in shape,
2) attached to said glove member,
3) contactable with said patient's hand when said patient's hand is placed within said glove member, and,
4) oriented such that a selected magnetic polarity is directed into said patient's hand.

9. The therapeutic apparatus according to claim 8,
a) wherein at least one of said at least two magnets contacts a lateral portion of a selected finger of said patient's hand when said patient's hand is placed within said glove member, and,
b) wherein at least one of said at least two magnets contacts a posterior portion of said patient's hand when said patient's hand is placed within said glove member.

10. The therapeutic apparatus according to claim 9 wherein said lateral portion includes a portion of an outer aspect of a little finger.

11. The therapeutic apparatus according to claim 9 wherein said lateral portion includes an inner aspect of the ring finger.

12. The therapeutic apparatus according to claim 8 wherein said at least two permanent magnets includes a first set of magnets and a second set of magnets and wherein, a) each of said first set of magnets are contactable with a posterior side of said patient's hand when said patient's hand is inserted into said glove member such that a first polarity is directed into the posterior side of said patient's hand; and,
b) each of said second set of magnets are contactable with an interior side of said patient's hand when said patient's hand is inserted into said glove member such that a second polarity is directed into the interior side of said patient's hand.

13. The therapeutic apparatus according to claim 12 wherein each of said first set of magnets is associated with one of said second set of magnets.

14. The therapeutic apparatus according to claim 8 wherein said at least two magnets includes a first magnet and a second magnet, and wherein:
a) said first magnet is contactable with an interior portion of a selected finger of said patient's hand when said patient's hand is inserted into said glove member such that a first polarity is directed into the interior portion of said patient's hand; and,
b) said second magnet is contactable with the interior portion of the selected finger of said patient's hand when said patient's hand is inserted into said glove member such that a second polarity is directed into the interior portion of said patient's hand.

15. The therapeutic apparatus according to claim 14 wherein said selected finger is the little finger.

16. The therapeutic apparatus according to claim 14 wherein said selected finger is the ring finger.

* * * * *